United States Patent [19]

Rohrbough

[11] Patent Number: 5,019,052

[45] Date of Patent: May 28, 1991

[54] BIPARTITE INJECTOR DEVICE

[75] Inventor: John Rohrbough, Walnut, Calif.

[73] Assignee: David Bull Laboratories Pty. Ltd., Mulgrave, Australia

[21] Appl. No.: 439,333

[22] Filed: Nov. 20, 1989

Related U.S. Application Data

[63] Continuation-in-part of Ser. No. 405,989, Sep. 12, 1989.

[51] Int. Cl.⁵ ............................................. A61M 5/24
[52] U.S. Cl. .................................................. 604/203
[58] Field of Search ............................ 604/86–91, 604/187, 200–205, 218, 234

[56] References Cited

U.S. PATENT DOCUMENTS

| | | | |
|---|---|---|---|
| 2,408,323 | 9/1946 | Lockhart | 604/201 X |
| 2,562,129 | 7/1951 | Scherer et al. | 604/203 |
| 3,523,531 | 8/1970 | Burke | 604/272 |
| 3,563,373 | 2/1971 | Paulson | 604/88 X |
| 3,570,486 | 3/1971 | Engelsher et al. | 604/88 |
| 3,768,474 | 10/1973 | Burke et al. | 604/205 X |
| 3,941,131 | 3/1976 | Ogle | 604/203 |
| 4,136,695 | 1/1979 | Dafoe | 604/203 X |
| 4,411,163 | 10/1983 | White | 73/864.02 |
| 4,713,062 | 12/1987 | Stevanato | 604/203 |
| 4,861,335 | 8/1989 | Reynolds | 604/88 |
| 4,886,495 | 12/1989 | Reynolds | 604/88 |

FOREIGN PATENT DOCUMENTS 2262534 9/1975 France ................ 604/205

Primary Examiner—John D. Yasko
Assistant Examiner—Adam J. Cermak
Attorney, Agent, or Firm—Darby & Darby

[57] ABSTRACT

Bipartite injector device formed of an outer shell having a front closed end with an external spout and an internal seat communicating by a bore, and a rear open end to receive the stoppered end of a medicament vial, and an inner sleeve having a front end for cantilever connection to the shell closed end, and a rear free end with a socket connectable to the vial stopper, plus a hollow needle having a front collar flange mountable via the sleeve to communicate with the bore at the seat and to dispose its rear pointed end in the socket to penetrate the stopper to connect the vial with the bore and spout. A circular rim on the sleeve exterior is compressed through a circular ring to reach a circular groove on the shell interior for snap fit cantilever locking therewith to provide a fluid tight coaxial and concentric arrangement of parts for flow between the vial and spout.

13 Claims, 3 Drawing Sheets

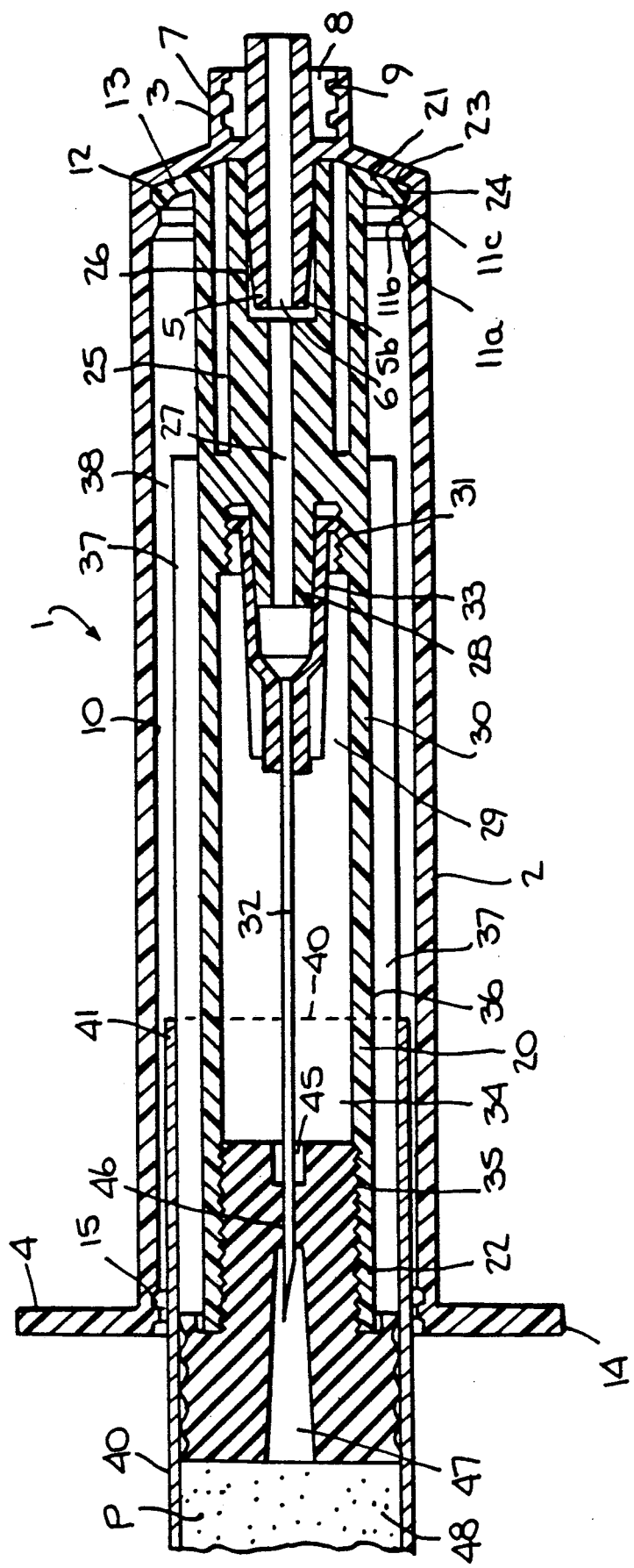

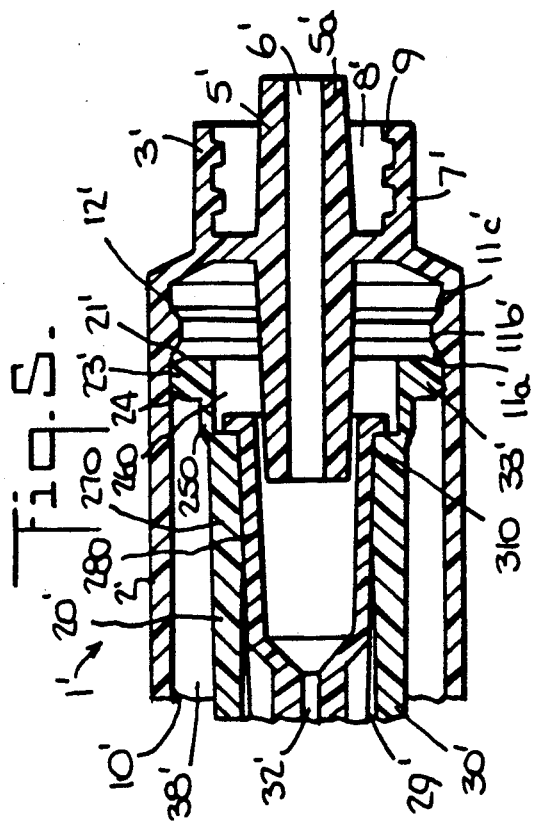
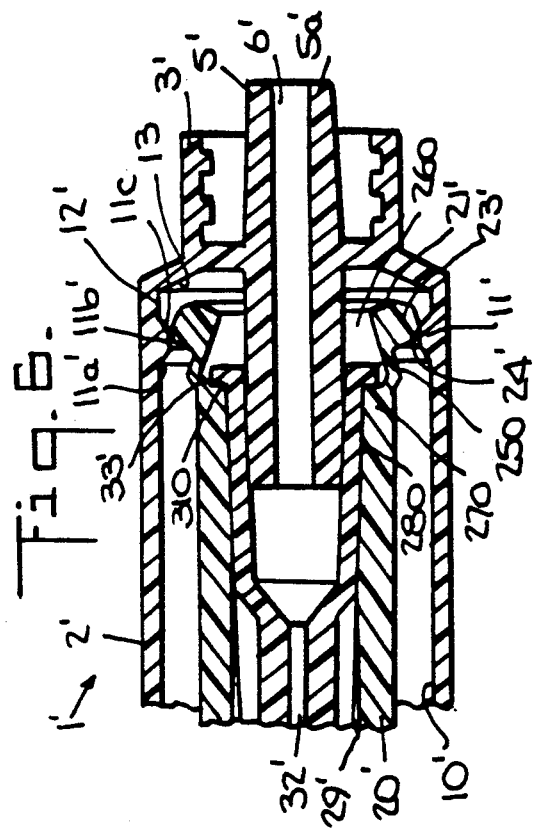
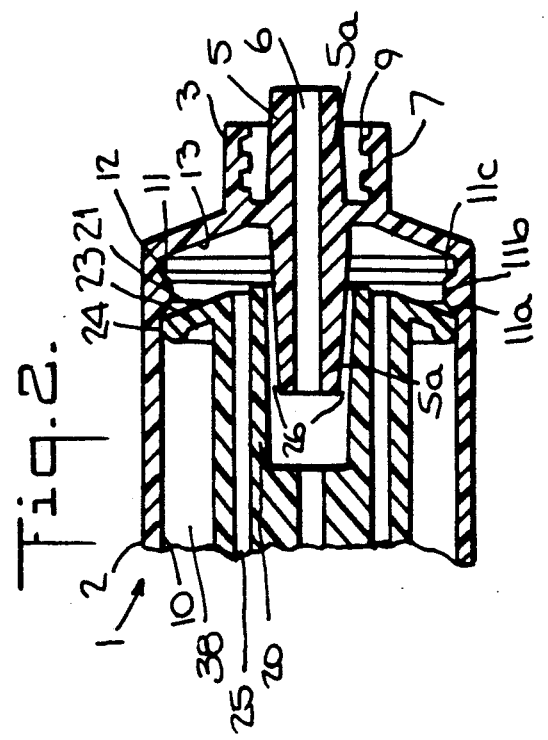
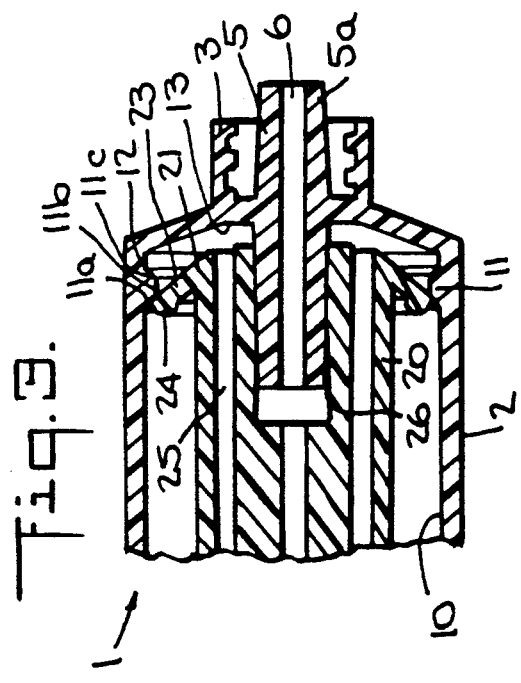

BIPARTITE INJECTOR DEVICE

CROSS-REFERENCE TO RELATED APPLICATION

This is a continuation-in-part of copending U.S. application Ser. No. 405,989 filed Sept. 12, 1989.

FIELD AND BACKGROUND OF THE INVENTION

The present invention relates to a bipartite injector device, and more particularly to such a device formed, of an outer shell having a closed end with a bore leading to an external spout, and an open end to receive the stoppered end of a medicament vial, and an inner sleeve having a cantilever end connectable to the shell closed end, and a free end with a socket connectable to the vial stopper, plus a hollow needle mountable at one end by the sleeve to communicate with the bore and to dispose its other pointed end in the socket to penetrate the stopper to communicate with the vial, the shell and sleeve having connector formations for coaxial snap fit cantilever interlocking and fluid tight flow connection of the parts.

This invention is a modification of that in copending U.S. application Ser. No. 405,989 filed Sept. 12, 1989, the disclosure of which is incorporated herein.

Briefly, said U.S. application Ser. No. 405,989 concerns a syringe mixer and injector device having an injector and an adapter with interconnectable nozzles on their facing ends and sockets in their remote ends flow connected by protected fluid pathways, and a tubular spike in each socket to penetrate the stopper of a vial when connected thereat, to charge the injector vial with the adapter vial contents, e.g. by one-way transfer, then disconnect the injector from the adapter and connect it directly and without modification to a dispensing device having a like connectable nozzle. The injector and adapter are each made as a unitary one-piece integral part.

Many syringe and/or injector constructions are known, as noted in said U.S. application Ser. No. 405,989, some having simple rib and groove or like interconnections of parts, e.g. as shown in U.S. Pat. Nos. 3,563,373 to Paulson and 3,570,486 to Engelsher et.al. Similar showings appear in U.S. Pat. Nos. 3,523,531 to Burke and 4,411,163 to White. However, the prior art does not appear to concern means permitting snap fit cantilever connection of parts for low cost production and assembly of accurately aligned and fluid tight interconnected yet separate pieces.

SUMMARY OF THE INVENTION

It is an object of the invention to provide a bipartite injector device formed of an outer shell and inner sleeve connected in cantilever manner to the shell for fluid tight flow of a medicament between a vial connected to one end of the device and a spout at the other end of the device, e.g. in turn connected to a separate charging or dispensing device.

It is another object of the invention to provide such a device which can be fabricated from conventional materials and components and assembled in simple and inexpensive manner.

According to the invention, a bipartite injector device is advantageously provided which comprises a longitudinal hollow outer shell and a separate cylindrical inner sleeve.

The shell has a front closed end, a rear open end and a cylindrical inner wall forming an interior to receive coaxially through the open end and guide for movement relative thereto a cylindrical medicament vial closed by a penetrable stopper. A central hub extends through the closed end from an external spout to a circular seat in the shell interior and has a bore extending from the spout to the seat. The shell has a radially inwardly directed circular constriction ring on the inner wall adjacent the closed end and a radially inwardly facing circular locking groove defined axially on the wall between the ring and closed end. The inner wall, ring, groove and seat are coaxial.

The sleeve has a front cantilever mounting end with a radially outwardly directed flange terminating peripherally in a circular compression rim, a central needle mounting portion and a rear free end having a cylindrical socket to connect the vial stopper stationarily thereat, and includes a hollow needle with a front circular collar flange and rear pointed end. The sleeve, rim, needle mounting portion and socket are coaxial.

The sleeve is sized for location in the shell sufficiently radially inwardly of the inner wall to permit insertion of the vial therebetween, and the rim is sized for compression displacement through the ring and snap fit locking in the groove to mount the sleeve coaxially in the shell with the sleeve front end in cantilever stationary connection with the shell closed end. The needle mounting portion is arranged to mount the needle coaxially and in fluid tight condition relative to the bore and sleeve to flow communicate the collar flange with the bore and to dispose the needle pointed end coaxially in the socket to penetrate the stopper for protected fluid tight flow between the vial and spout through the needle and bore.

The shell has a radial front wall forming its closed end, and the sleeve flange is preferably sized and arranged to abut that wall when the rim and groove are in locking engagement.

According to one feature, the needle mounting portion has a forwardly facing central circular recess at the sleeve front end, a rearwardly facing central circular extension and a passage from the recess to the extension, the recess, extension and rim being coaxial. The collar flange is arranged for coaxial mounting on the extension, and the recess is arranged to receive the seat coaxially. The needle mounting portion has connector means and the collar flange has counterpart connector means to connect the needle to the sleeve at the extension.

The sleeve may have an annular excavation radially between its flange and recess and extending from its front end toward its extension to define a concentric compression compensation space to aid local compression displacement of the rim through the ring for snap fit locking in the groove.

Per an alternative feature, the needle mounting portion has a central circular hollow recess formation with a circular shoulder, the formation, shoulder and rim being coaxial, and the formation and shoulder sized to receive and engage the collar flange with the formation peripherally embracing it and the shoulder axially locating it to mount it on the seat.

The recess formation includes a forwardly facing larger diameter central circular neck recess at the sleeve front end outwardly bounded by a forward thin wall neck extending rearwardly from the sleeve flange, and a rearwardly facing smaller diameter central circular shank recess outwardly bounded by a thick wall shank extending rearwardly from, and separated by the shoulder from, the neck. The shoulder is arranged to locate the collar flange rearwardly of the forward-most neck extent, and the neck is sized to aid the rim compression displacement through the ring to lock in the groove.

The shell has a nozzle outwardly confining the spout at its closed end to connect thereto a separate charging or dispensing device for fluid tight flow between the vial and separate device via the needle and spout. The nozzle may have a luer lock connector mating with a counterpart connector on the separate device for their releasable interconnection. The socket has threads mating with those on the vial stopper.

Preferably, the shell and sleeve are plastic, e.g. formed as injection molded pieces, for snap fit cantilever connection to provide the bipartite device, and the needle is metal.

Broadly, the shell and sleeve have coacting circular connector formations for snap fit cantilever interlocking.

BRIEF DESCRIPTION OF THE DRAWINGS

Other objects of the invention will become apparent from the within specification and accompanying drawings, in which:

FIG. 1 is a schematic sectional view of a bipartite injector device according to one, e.g. large size, embodiment of the invention, with a medicament vial connected thereto;

FIGS. 2 and 3 are exaggerated partial views of the FIG. 1 device, showing the snap fitting of the sleeve to the shell;

FIGS. 5 and 6 are similar to FIGS. 2 and 3, but show the snap fitting of the sleeve to the shell of the FIG. 4 device.

DESCRIPTION OF THE PREFERRED EMBODIMENTS

Figure 4:
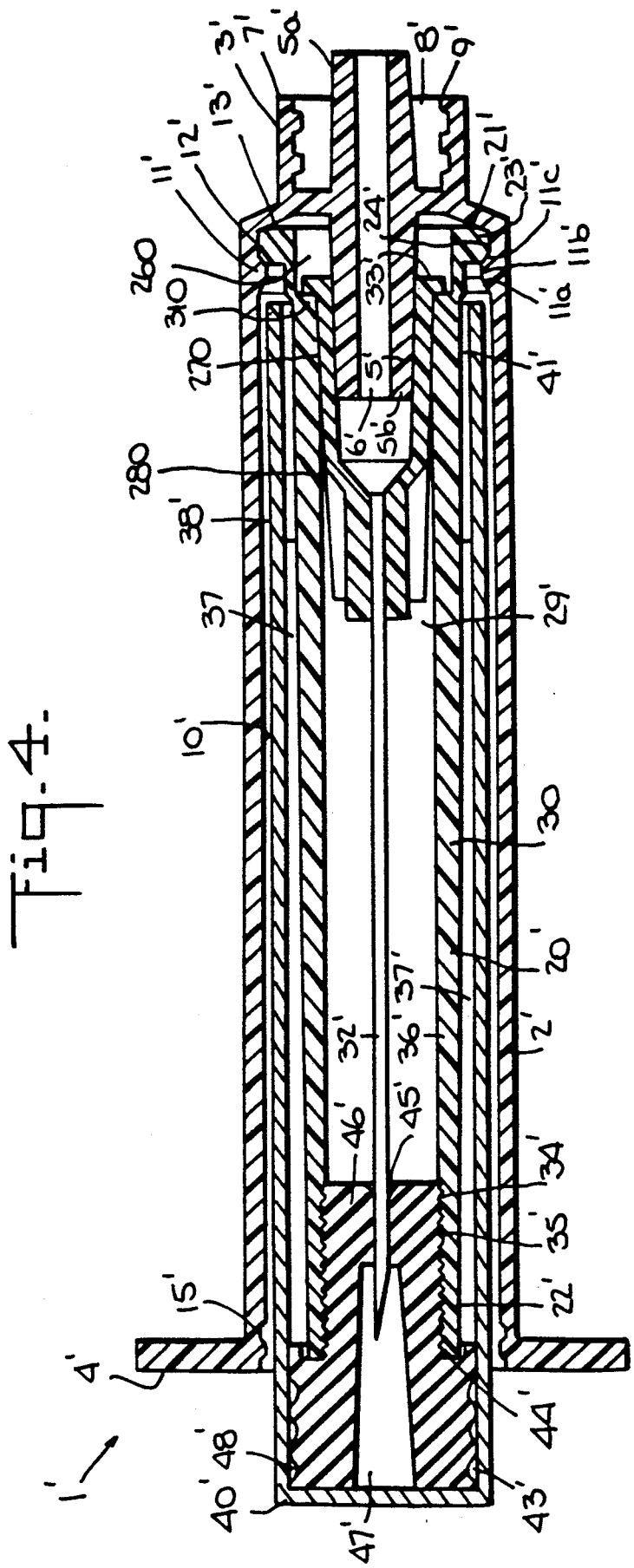
FIG. 4 is a schematic sectional view of a bipartite injector device according to another, e.g. small size, embodiment of the invention, with such a vial connected thereto.

Referring to the drawings, and initially to FIG. 1, a bipartite injector device 1 is shown, including a longitudinal, e.g. cylindrical, hollow outer shell 2 and a cylindrical inner sleeve 20, plus a conventional cylindrical medicament powder or liquid containing receiving vial in the form of a plunger vial 40 at the rear end of device 1. Such may be used with an adapter connectable to the front end of device 1 and having its own medicament liquid containing charging vial (not shown), as described more fully in said U.S. application Ser. No. 405,989.

Shell 2 has a front closed end 3, a circular rear open end 4 and a circular central hub 5. Hub 5 extends through closed end 3 from its external circular, e.g. tapered, spout 5a to its internal circular, e.g. tapered, seat 5b in the shell interior, and has a central bore 6 extending internally from spout 5a to seat 5b. An external nozzle 7 at closed end outwardly confines spout 5a and has a recess 8 provided with a connector, e.g. a conventional luer lock such as male luer lock 9, to connect nozzle 7 to a separate device having a counterpart connector, such as a female luer lock, e.g. a charging device formed of an adapter connected to a charging vial or a dispensing device such as an injection needle (not shown).

Cylindrical inner wall 10 of shell 2 forms an interior to receive coaxially via end 4 and guide vial 40 for relative longitudinal and rotational movement, whose open end 41 is closed by shiftable cylindrical, needle penetrable, stopper 42 having rings 43 to seal its, e.g. powder, medicament P content.

Inner wall 10 has a radially inwardly directed circular constriction ring adjacent closed end 8 and a radially inwardly facing circular locking groove 12 defined axially thereon between ring 11 and the radial front wall 13 forming closed end 3. Ring 11 is formed of a hollow, e.g. about 30 degree angle, frustoconical insert ramp 11a, a hollow cylindrical center span 11b, and an opposed hollow, e.g. about 45 degree angle, frustoconical lock ramp 11c.

Wall 10, ring 11, groove 12 and seat 5b are circular in cross section, concentric and coaxial, and bore 6 extends along the center axis of shell 2.

Rear end 4 has lateral flanges 14 formed as finger grips to aid handling of device 1 in use, and a groove formation 15 to receive an aseptic friction fit closure cap (not shown) to keep device 1 sterile before use with vial 40. A similar cap (not shown) protects spout 6 and nozzle 7 at front end 3.

Sleeve 20 has a front cantilever mounting end 21 and a rear free end 22. Front end 21 has a radially outwardly directed circular flange 23 terminating peripherally in a circular compression rim 24, sized and arranged to coact with ring 11 and groove 12 to connect front end 21 of sleeve 20 in cantilever manner to front end 3 of shell 2. Front end 21 also has an annular excavation 25 and a forwardly facing central circular, e.g. tapered, recess 26 communicating via central internal passage 27 with a rearwardly facing central circular, e.g. tapered, extension 28.

Excavation 25 is located radially between flange 28 and recess 26, extending from front end 21 toward extension 28 to define a concentric compression compensation space to aid local compression displacement of rim 24 through ring 11 for snap fit locking in groove 12. Recess 26 is sized and arranged to receive seat 5b of hub 5 in fluid tight condition to communicate bore 6 with passage 27. The remainder of the sleeve 20 interior at extension 28 forms an annular space 29 within rearward cylindrical extension 30 having internal threads 31.

Hollow needle 32, e.g. a conventional standard, regular bevel (B-D I.V. 166A×1½") metal needle, is disposed in cylindrical extension 30 with its externally threaded front circular, e.g. tapered, collar flange 33 mounted in fluid tight condition on central extension 28 via internal threads 31 on extension 30 at annular space 29, to communicate with passage 27. This mounting also positions the rear pointed end of needle 32 coaxially in socket 34, in rear end 22 at the remote portion of extension 30, and centrally of socket internal threads 85, within sleeve circular outer wall 86.

Rim 24, space 25, recess 26, extension 28, space 29, extension 30, socket 34 and outer wall 36 are circular in cross section, concentric and coaxial, and passage 27 extends along the center axis of sleeve 20.

Recess 26, central extension 28, space 29 and cylindrical extension 30 provide a central needle mounting portion between rim 24 and socket 34, so that when rim 24 firmly locks in groove 12, recess 26 automatically firmly seats against seat 5b, and threads 31 selectively adjustably engaging threaded collar flange 33 automatically locate needle 32 to seat flange 83 automatifirmly against extension 28, for fluid tight flow between needle 32 and spout 5a via passage 27 and bore 6.

Matching tapers for seat 5b, recess 2G, extension 2B and collar flange and preset positioning of needle 32 per threaded collar flange 33 and threads 31, assure fluid tight connection of the pertinent needle 32 and sleeve 20 portions, as rim 24, ring 11 and groove 12 are sized, located and matched for tight snap fit connection of sleeve 20 to shell 2.

As shown in FIGS. 2-3, rim 24 is precisely sized for compression displacement through ring 11 and snap fit locking in groove 12, so that sleeve 20 may be readily connected to shell 2 by unskilled labor. As these two pieces are moved increasingly telescopingly together, e.g. under manual force using a simple jig, rim 24 is compressed against, e.g. 30 degree, shallow incline insert ramp 11a, promoting its movement to and across cylindrical span 11b, aided by space 25 to permit compensating radially inward temporary deformation of rim 24 and flange 23, due to the inherent resiliency of the material, e.g. plastic, of which sleeve 20 is made.

When rim 24 reaches, e.g. 45 degree, steep incline lock ramp 11c, its snap fit movement into groove 12 is assisted, since its loaded compression force is rapidly released along ramp 11c as it expands to its original radial dimension and tightly and firmly stationarily engages groove 12, as shown in FIG. 1. By conforming front end 21 of sleeve 20 at flange 23 to the counterpart internal shape of front end 3 of shell 2 at radial wall 13, by appropriate sizing and shaping of these parts, they may be placed in firm stationary abutment with flange 23 acting against wall 13 under the snap fit cantilever locking connection force between rim 24 and groove 12.

Thus, ring 11 and groove 12 form a circular snap fit cantilever connector formation in shell 2 adjacent closed end and flange 23 and rim 24 form a counterpart snap fit cantilever connector formation on sleeve front end 21, the two formations being sized and arranged for snap fit interlocking to mount sleeve 20 coaxially in shell 2 with front end 21 in cantilever stationary connection with closed end 3.

Shell 2 and sleeve 20 are preferably formed as injection molded plastic pieces, to promote their snap fit cantilever locking and fluid tight connection, and enable use of low cost dies of simple design, yet of precise dimension and shape, to fabricate these two pieces with conforming parts accurately mating to achieve their desired concentric and coaxial alignment relationship that is essential to proper alignment with vial 40 during use. For example, shell 2 and sleeve 20 may be sized for 10 mL to 50 mL dosages with concordantly sized vials.

As shown in FIG. 1, internal threads in socket 84 connect stopper 42 of vial 40 stationarily thereat when open end 41 is screwed therein via stopper external threads 44. This causes the pointed end of needle 32 to align coaxially with stopper entrance 45, penetrate seal 46, enter stopper bore 47 and flow communicate with vial chamber 48. By grasping flanges 14, vial 40 may be pushed between shell inner wall 10 and sleeve outer wall 36, preferably having circumferentially spaced longitudinal guide ribs 37, along guideway 38.

Ribs 37 selectively radially size the annular gap of guideway 8B, i.e. between the outer radius of sleeve ribs 37 and inner radius of shell wall 10, to conform to the vial 40 radial dimensions, while conserving material and lightening the structure without detracting from the robust structural integrity of sleeve 20, in that the circumferential arc portions between ribs 37 constitute excavated spaces on outer wall 86. Ribs 37 inhibit wobble between shell 2, sleeve 20 and vial 40, and misalignment between needle 82 and stopper entrance 45.

A larger size device 1 may be used for a smaller size dosage in appropriate cases, as by using a 10 mL size device 1 with a half filled 10 mL size vial 40, i.e. having 5 mL of medicament P. e g. with stopper 42 shifted half way into open end 41, to eliminate the need for a 5 mL mize device 1 (and closure caps) and a 5 mL size vial 40 and stopper 42. End 41 of the half filled vial 40 may be closed by a cap, similar to the use of caps to cover open end 4 and nozzle 7 and spout 5a.

When the half filled vial is inserted in guideway 38 and stopper 42 screwed into socket 34 to cause needle 32 to enter stopper entrance 45 and puncture seal 46, vial 40 may be pushed further into device 1 while stopper 42 is stationarily connected to socket 34, to force medicament P from the filled rear half of vial 40 via needle 32, passage 27 and bore 6 to spout 5b, e.g. when connected to a separate dispensing device.

FIGS. 4-6 show an alternative embodiment in which analogous parts to those of FIGS. 1-3 have prime (') designations. While device 1 of FIGS. 1-3 is used in large dosage sizes, device 1' of FIGS. 4-6 is used in smaller sizes, e.g. for 0.5 mL to 3 mL dosages, with needle 32' being an analogous standard, regular bevel (B-D I.V. 196A×1¼") metal needle, and shell 2' and sleeve 20' plastic, e.g. injection molded, pieces.

Device 1' has a shell 2' of parts 3' to 15' and a sleeve 20' of parts 21' to 24', 29' to 30' and 32' to 38', generally the same as those of device 1, but of smaller size, for use with an analogous vial 40' of parts 41' to 48' generally the same as those of vial 40, but of concordantly smaller size. However, the needle mounting portion of sleeve 20' is modified relative to the analogous parts of device 1, as device 1' is of such small size that it would be too difficult and costly in practice to provide it with the construction of device 1.

Device 1' has a needle mounting portion with an enlarged central circular hollow recess formation and circular shoulder that are coaxial with rim 24' and sized to receive and engage collar flange 33' with the recess formation peripherally embracing flange 33' and the shoulder axially locating it to mount it directly on seat 5b'. The recess formation includes a forwardly facing larger diameter central circular neck recess 260 at sleeve front end 21' outwardly bounded by a forward thin wall cylindrical neck 250 extending rearwardly from sleeve flange 23', and a rearwardly facing smaller diameter central circular shank recess 280 outwardly bounded by a thick wall cylindrical shank 270 extending rearwardly from neck 250 and separated therefrom by shoulder 310.

As shown in FIG. 4, neck recess 260, shank 270, shank recess 280 and shoulder 310 are sized and arranged to locate collar flange 83' axially rearwardly of the forward-most extent of neck 250 in fluid tight fit directly on and against seat 5b' to communicate needle 32' with shell bore 6', analogous to recess 26, passage 27, extension 28 and threads 31 of device 1.

As shown in FIGS. 5-6, neck 250 is sized to aid local compression displacement of rim 24' through ring 11' for snap fit locking in groove 12', analogously to space 25 of device 1.

By precise sizing of neck 250, shoulder 310 and shank 270, and thus of recess 260 and recess 280, relative to collar flange 88', and of rim 24' relative to groove 12' and seat 5b', when rim 24' locks in groove 12' collar flange 33' automatically seats firmly against seat 5b' and is held thereat by shank 270 and shoulder 310 connected via neck 250 with rim 24', acting in one axial direction thereagainst, and by seat 5b' acting in the opposite axial direction thereagainst.

In both devices 1 and 1', when the vial is screwed into the socket, the pushing and rotational movement of the vial inhibits possible rotation of the sleeve relative to the shell, as this movement applies friction force urging the rim against the groove and the flange against the radial wall.

In device 1, this force also urges recess 26 against seat 5b and needle 32 against extension 28 for like inhibition of possible rotation of sleeve 20 and needle 32. In device 1', this force also urges shank 270 and shoulder 810 against collar flange 33' and the latter against seat 5b', at the same time preventing axial compression of thin wall neck 250. Neck 250 is sufficiently thick to withstand axial tension between rim 24' and shoulder 310 in keeping collar flange 33' on seat 5b'.

Thus, the construction of devices 1 and 1' permits their low cost fabrication and their low cost manual assembly by unskilled labor into a bipartite unit composed of two individual and separate pieces, interconnected by snap fit, and not welded or otherwise integrally interconnected, and incorporating therewith a standard commercially available type needle.

The parts of the two separate pieces are precisely formed, sized, shaped and arranged, relative to each other to maintain their snap fit cantilever interconnection, with their parts in accurate centered alignment, and especially with the given, i.e. cantilever mounted, standard needle centered relative to the sleeve socket, which centering is critical for vial stopper center puncturing without misalignment or other mishap, especially in an emergency when medicament charging, transfer and/or dispensing, e.g. via separate standard charging and/or dispensing devices, must be effected rapidly and safely both as regards the patient and the user of the device.

The parts are desirably sized to position the needle pointed end coaxially in the socket slightly inwardly of the sleeve open end sufficiently to protect the needle from unintended human contact thereat. Due to the precise fluid tight fit of the associated internal parts of device 1 and device 1', the flow path from the vial through the needle via passage 27 and bore 6 in device 1, or via bore 6 alone in device 1', is completely protected and entirely free of dead spaces. Devices 1 and 1' may be provided as one-time use discardable items.

Since in devices 1 and 1' the ring and groove are formed on the shell, and the flange and rim are formed on the sleeve, as integral parts, they will be more precisely centered and axially positioned, e.g. to tolerances controlled by the injection molding process, for more accurate coaxial alignment of the needle mounted thereon with the stopper entrance of the vial, to achieve easy, rapid and safe screwing of the stopper into the socket without needle and stopper bore misalignment.

On the other hand, once off center, as the vial stopper is rotated into the socket, the needle will bury itself into the thick sidewall of the stopper and not flow connect with the vial contents, thereby rendering the unit inoperable, a result to be avoided in attempting an emergency injection. Use of extra force to achieve flow connection in such case raises the added risk of shattering the vial and injuring the user's hand.

The specification and drawings are set forth by way of illustration and not limitation, and various modifications and changes may be made therein without departing from the spirit and scope of the invention which is to be limited solely by the scope of the claims.

What is claimed is:

1. Bipartite injector device comprising
   a longitudinal hollow outer shell having a central axis and including a front closed end formed by a generally radial front wall, a rear open end, a cylindrical inner wall forming an interior adapted to receive coaxially through the open end and guide for movement relative thereto a cylindrical medicament vial closed by a penetrable stopper, a central hub extending through the closed end from an external hub spout to an internal hub circular seat in the shell interior and having a bore extending therethrough from the spout to the seat, a radially inwardly directed circular constriction ring on the inner wall adjacent the closed end and a radially inwardly facing circular locking groove defined axially on the inner wall between the ring and the radial front wall forming the closed end, the inner wall, ring, groove and seat being coaxial relative to the shell central axis,
   a cylindrical inner sleeve having a central axis and including a front cantilever mounting end having a radially outwardly directed flange terminating peripherally in a circular compression rim, a central needle mounting portion and a rear free end having a cylindrical connection socket adapted to connect stationarily such stopper thereat, and a hollow needle having a front circular collar flange and a rear pointed end, the sleeve, rim, needle mounting portion and socket being coaxial relative to the sleeve central axis,
   the sleeve being sized for location in the shell sufficiently radially inwardly of the inner wall to permit insertion of the vial therebetween, the rim being sized for compression displacement through the ring and snap fit locking in the groove to mount the sleeve coaxially in the shell with the sleeve front end in cantilever stationary connection with the shell closed end, the sleeve flange being sized and arranged to abut stationarily against the radial front wall forming the shell closed end when the rim is in snap fit locking engagement with the groove, and the needle mounting portion being arranged to mount the needle coaxially and in fluid tight condition relative to the bore and sleeve to flow communicate the collar flange with the bore and to dispose the needle pointed end coaxially in the socket to penetrate such stopper for protected fluid tight flow between the vial and spout through the needle and bore.

2. Device of claim 1 wherein the needle mounting portion includes a forwardly facing central circular recess at the sleeve front end, a rearwardly facing central circular extension and a passage extending therethrough from the recess to the extension, the recess, extension and rim being coaxial, the collar flange being arranged for coaxial mounting on the extension, and the recess being arranged to receive the seat coaxially.

3. Device of claim 2 wherein the needle mounting portion has connector means adjacent the extension and the collar flange has counterpart connector means to connect the needle to the sleeve at the extension.

4. Device of claim wherein the sleeve has an annular excavation radially between the sleeve flange and recess and extending from the sleeve front end toward the extension to define a concentric compression compensation space to aid local compression displacement of the rim through the ring for snap fit locking in the groove.

5. Device of claim 1 wherein the needle mounting portion includes a central circular hollow recess formation having a circular shoulder, the recess formation, shoulder and rim being coaxial, and the recess formation and shoulder being sized to receive and engage the collar flange with the recess formation peripherally embracing the collar flange and the shoulder axially locating the collar flange to mount the collar flange directly on the seat.

6. Device of claim 5 wherein the recess formation includes a forwardly facing larger diameter central circular neck recess at the sleeve front end outwardly bounded by a forward thin wall neck portion extending rearwardly from the sleeve flange, and a rearwardly facing smaller diameter central circular shank recess outwardly bounded by a thick wall shank portion extending rearwardly from the neck portion and separated therefrom by the shoulder, the shoulder being arranged to locate axially the collar flange rearwardly of the forwardmost extent of the neck portion, and the neck portion being sized to aid local compression displacement of the rim through the ring for snap fit locking in the groove.

7. Device of claim 1 wherein the shell has an external nozzle at its closed end outwardly confining the spout and arranged to connect a separate charging or dispensing device thereto for fluid tight flow between the vial and that separate device through the needle and spout.

8. Device of claim 7 wherein the nozzle has a luer lock connector to mate with a counterpart luer lock connector on that separate device for releasable interconnection thereof.

9. Device of claim 1 wherein the socket has internal thread means to mate with counterpart external thread means on the stopper of the corresponding vial to be connected thereto.

10. Device of claim 1 wherein the shell and sleeve are formed of plastic for snap fit cantilever connection to provide the bipartite device.

11. Device of claim 11 wherein the shell and sleeve are formed as injection molded pieces.

12. Device of claim 10 wherein the needle is metal.

13. Bipartite injector device comprising
a longitudinal hollow outer shell having a central axis and including a front closed end formed by a generally radial front wall, a rear open end, a cylindrical inner wall forming an interior adapted to receive coaxially through the open end and guide for movement relative thereto a cylindrical medicament vial closed by a penetrable stopper, a central hub extending through the closed end from an external hub spout to an internal hub circular seat in the shell interior and having a bore extending therethrough from the spout to the seat, and a circular snap fit cantilever connector formation in the shell interior adjacent the radial front wall forming the closed end, the inner wall, connector formation and seat being coaxial relative to the shell central axis, and
a cylindrical inner sleeve having a central axis and including a front cantilever mounting end having a counterpart circular snap fit cantilever connector formation, a central needle mounting portion and a rear free end having a cylindrical connection socket adapted to connect stationarily such stopper thereat, and a hollow needle having a front circular collar flange and a rear pointed end, the sleeve, counterpart connector formation, needle mounting portion and socket being coaxial relative to the sleeve central axis,
the sleeve being sized for location in the shell sufficiently radially inwardly of the inner wall to permit insertion of the vial therebetween, the connector formation and counterpart connector formation being sized and arranged for snap fit interlocking to mount the sleeve coaxially in the shell with the sleeve front end in cantilever stationary connection with the shell closed end, the connector formation being sized and arranged to abut stationarily against the radial front wall forming the shell closed end when the connector formation is in snap fit locking engagement with the counterpart connector formation, and the needle mounting portion being arranged to mount the needle coaxially and in fluid tight condition relative to the bore and sleeve to flow communicate the collar flange with the bore and to dispose the needle pointed end coaxially in the socket to penetrate such stopper for protected fluid tight flow between the vial and spout through the needle and bore.

* * * * *